US00PP22315P2

(12) United States Plant Patent
Hooijman

(10) Patent No.: US PP22,315 P2
(45) Date of Patent: Dec. 13, 2011

(54) ROSE PLANT NAMED 'ESM R001'

(50) Latin Name: *Rosa hybrida*
Varietal Denomination: Esm R001

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 12/927,781

(22) Filed: Nov. 22, 2010

(51) Int. Cl.
*A01H 5/00* (2006.01)

(52) U.S. Cl. ..... Plt./104

(58) Field of Classification Search ..... Plt./104
See application file for complete search history.

*Primary Examiner* — Kent L Bell
(74) *Attorney, Agent, or Firm* — C. A. Whealy

(57) ABSTRACT

A new and distinct cultivar of Rose plant named 'Esm R001', characterized by its strong and upright flowering stems; vigorous growth habit; durable leaves; large intense yellow-colored flowers; good postproduction longevity; and resistance to Botrytis.

1 Drawing Sheet

Botanical designation: *Rosa hybrida.*
Cultivar denomination: 'ESM R001'.

BACKGROUND OF THE INVENTION

The present Invention relates to a new and distinct cultivar of Rose plant, botanically known as *Rosa hybrida,* commercially used as a cut flower Rose plant, and hereinafter referred to by the name 'Esm R001'.

The new Rose plant is a product of a planned breeding program conducted by the Inventor in El Quinche, Pichincha, Ecuador. The objective of the breeding program was to develop new freely-flowering cut flower Rose varieties with novel and attractive flower colors and excellent postproduction longevity.

The new Rose plant originated from a cross-pollination made by the Inventor in March, 2005 of a proprietary Rose selection identified as code name Line 13, not patented, as the female, or seed, parent with a proprietary Rose selection identified as code name Line 183, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in January, 2006.

Asexual reproduction of the new Rose plant by cuttings at El Quinche, Pichincha, Ecuador since October, 2006, has shown that the unique features of this new Rose plant are stable and reproduced true to type in successive generations of asexual reproduction.

SUMMARY OF THE INVENTION

Plants of the new Rose have not been observed under all possible environmental conditions. The phenotype may vary somewhat with variations in environment such as temperature and light intensity, without, however, any variance in genotype.

The following traits have been repeatedly observed and are determined to be the unique characteristics of 'Esm R001'. These characteristics in combination distinguish 'Esm R001' as a new and distinct Rose plant:

1. Strong and upright flowering stems.
2. Vigorous growth habit.
3. Durable leaves.
4. Large intense yellow-colored flowers.
5. Good postproduction longevity.
6. Resistant to Botrytis.

Plants of the new Rose differ from plants of the female parent selection in the following characteristics:

1. Plants of the new Rose are smaller than plants of female parent selection.
2. Plants of the new Rose have smaller flowers than plants of the female parent selection.
3. Plants of the new Rose and the female parent selection differ in flower color as plants of the female parent selection have light yellow-colored flowers.

Plants of the new Rose differ from plants of the male parent selection in the following characteristics:

1. Plants of the new Rose are taller than plants of the male parent selection.
2. Plants of the new Rose have larger flowers than plants of the male parent selection.
3. Plants of the new Rose and the male parent selection differ in flower color as plants of the male parent selection have light yellow-colored flowers.

Plants of the new Rose can be compared to plants of Rose 'Golden Gate', not patented. In side-by-side comparisons conducted in El Quinche, Pichincha, Ecuador, plants of the new Rose differed from plants of 'Golden Gate' in the following characteristics:

1. Plants of the new Rose were more vigorous and larger than plants of 'Golden Gate'.
2. Plants of the new Rose had thicker and stronger stems than plants of 'Golden Gate'.
3. Plants of the new Rose had larger leaves than plants of 'Golden Gate'.
4. Plants of the new Rose had larger flowers than plants of 'Golden Gate'.
5. Flowers of plants of the new Rose were longer lasting than flowers of plants of 'Golden Gate'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the left of the sheet comprises a side perspective view of a typical flowering stem of 'Esm R001'.

The photograph at the upper right of the sheet is a close-up view of a typical flower of 'Esm R001'.

The photograph at the bottom left of the sheet is a close-up view of typical flowers of 'Esm R001'.

The photographs at the lower right of the sheet are close-up views of the upper and lower surfaces of typical leaves of 'Esm R001'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown in 10-cm containers in a polyethylene-covered greenhouse in El Quinche, Pichincha, Ecuador and under typical hydroponic Rose production practices. Plants were pinched about 13 to 14 weeks after planting. Plants were 2.5 years old when the photographs and description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'Esm R001'.

Parentage:

*Female, or seed, parent.*—Proprietary seedling selection of *Rosa hybrida* identified as code name Line 13, not patented.

*Male, or pollen, parent.*—Proprietary seedling selection of *Rosa hybrida* identified as code name Line 183, not patented.

Propagation:

*Type.*—By cuttings.

*Time to initiate roots.*—About seven to ten days at 26° C. to 30° C.

*Time to produce a rooted young plant.*—About four to five weeks at 22° C. to 26° C.

*Root description.*—Fibrous, medium in thickness; close to 200A and N200A in color.

*Rooting habit.*—Freely branching; dense.

Plant description:

*Plant form.*—Upright plant habit; strong and upright flowering stems.

*Growth habit.*—Vigorous; freely basal branching habit; dense and bushy growth habit; about twelve flowering stems develop per year.

*Plant height.*—About 79 cm.

*Plant width (spread).*—About 55 cm.

*Lateral branches (peduncles).*—Length: About 79 cm. Diameter: About 6.4 mm. Internode length: About 5.8 cm. Texture: Smooth, glabrous. Color: Close to 147A tinged with close to 200B. Thorns: Density: High. Shape: Triangular with sharp acuminate apices; slightly incurved. Height: About 1.2 cm. Length, at base: About 1.2 cm. Color, immature: Close to 146C tinted with close to 187B. Color, mature: Close to 183A.

Foliage description:

*Arrangement.*—Alternate; compound with typically five to seven leaflets per leaf.

*Leaf length.*—About 16.8 cm.

*Leaf width.*—About 13.9 cm.

*Terminal leaflet length.*—About 8.1 cm.

*Terminal leaflet width.*—About 5.6 cm.

*Lateral leaflet length.*—About 6.6 cm.

*Lateral leaflet width.*—About 4.9 cm.

*Leaflet shape.*—Oval.

*Leaflet apex.*—Acute.

*Leaflet base.*—Attenuate.

*Leaflet margin.*—Serrate.

*Leaflet texture, upper and lower surfaces.*—Smooth, glabrous.

*Leaflet venation pattern.*—Pinnate.

*Leaflet color.*—Developing leaflets, upper surface: Close to 146A; towards the margins, close to 178A. Developing leaflets, lower surface: Close to 146A tinted with close to N199A. Fully expanded leaflets, upper surface: Close to 136A and 139A; venation, close to 199A. Fully expanded leaflets, lower surface: Close to 147B; venation, close to 146D.

*Petioles, leaves.*—Length: About 1.6 cm. Diameter: About 2 mm. Texture, upper and lower surfaces: Smooth, glabrous. Color, upper surface: Close to 199A. Color, lower surface: Close to 146A tinted with close to N199B.

*Petioles, leaflets.*—Length: About 2.4 cm. Diameter: About 1.4 mm. Texture, upper and lower surfaces: Smooth, glabrous. Color, upper surface: Close to 146B to 146C tinted with close to 199A. Color, lower surface: Close to 144A.

*Stipules.*—Arrangement and appearance: Two, adnate to the petiole, leafy. Length: About 2.6 cm. Width: About 3 mm. Shape: Roughly deltoid. Apex: Acuminate. Base: Truncate. Margin: Serrate, irregular. Texture, upper and lower surfaces: Smooth, glabrous; pubescent along the margins. Venation pattern: Pinnate. Color, upper surface: Close to 146A and 147A. Color, lower surface: Close to 146A.

Flower description:

*Flower type and habit.*—Symmetrical rosette flowers; typically grown as a single stem.

*Flowering season.*—Year-round under greenhouse conditions, plants begin flowering about 65 to 67 days after pinching; in the garden, optimal flowering from spring through autumn; flowering intermittent.

*Flower diameter.*—About 12 cm.

*Flower depth (height).*—About 6 cm.

*Flower longevity on plant.*—About 22 days; flowers persistent.

*Flower longevity as a cut flower.*—About eleven to twelve days.

*Fragrance.*—Moderately fragrant, pleasant.

*Flower buds.*—Shape: Cupped. Length: About 5.5 cm. Diameter: About 4 cm. Color: Close to 144A tinted with close to N199D.

*Petals.*—Quantity: About 34 per flower; petals imbricate. Length: About 5.8 cm. Width: About 5.7 cm. Shape: Nearly round; transversely ovate. Apex: Blunt to short acute. Base: Obtuse. Margin: Entire. Texture, upper and lower surfaces: Smooth, glabrous; papery to coriaceous. Color: When opening and fully opened, upper surface: Close to 14A. When opening and fully opened, lower surface: Close to 13A.

*Sepals.*—Quantity per flower: Typically five. Length: About 5.6 cm. Width: About 1.4 cm. Shape: Roughly deltoid. Apex: Tapered. Base: Truncate. Margin: Entire; ciliate. Texture, upper and lower surfaces: Pubescent; coriaceous. Color: When opening, upper surface: Close to 146B to 146D. When opening, lower surface: Close to 146B tinted with close to N199D. Fully opened, upper surface: Close to 146A to 146D. Fully opened, lower surface: Close to 143A and 145A.

*Reproductive organs.*—Stamens: Quantity: About 129 per flower. Anther length: About 3.6 mm. Anther shape: Reniform. Anther color: Close to 163B and 162D. Filament color: Close to 14A. Pollen amount: Scarce. Pollen color: Close to N163D. Pistils: Quantity: About 94 per flower. Pistil length: About 1.9 cm. Stigma shape: Broadly reniform. Stigma color: Close to 153D. Style length: About 1.2 cm. Style color: Close to 151D. Receptacle height: About 1.1 cm. Receptacle diameter: About 1.4 cm. Receptacle shape: Cup-shaped. Receptacle texture: Smooth, glabrous. Receptacle color: Close to 144A. Fruits: Length: About 3.3 cm. Diameter: About 2.5 cm. Texture: Smooth. Color: Close to 11A becoming closer to 152D with development. Seeds: Quantity per fruit: About one or two. Length: About 7 mm. Diameter: About 5 mm. Texture: Smooth. Color: Close to 153D.

Pathogen/pest resistance: Plants of the new Rose have been observed to be resistant to Botrytis. Plants of the new Rose have not been observed to be resistant to pests and other pathogens common to Roses.

Temperature tolerance: Plants of the new Rose have been observed to tolerate temperatures ranging from 0° C. to 35° C.

It is claimed:

1. A new and distinct Rose plant named 'Esm R001' as illustrated and described.

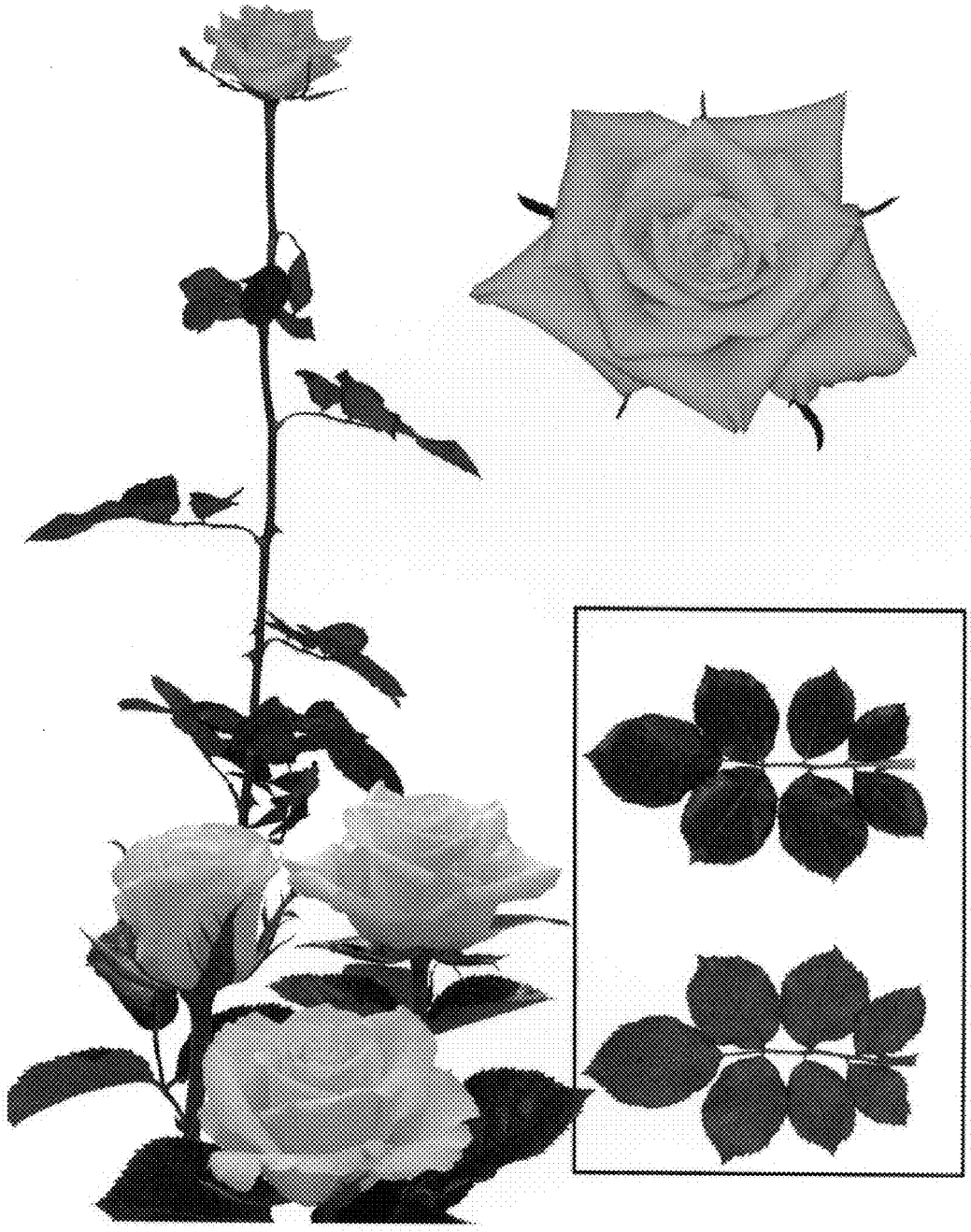

* * * * *